United States Patent [19]

Cawood

[11] Patent Number: 5,463,712

[45] Date of Patent: Oct. 31, 1995

[54] FIBEROPTIC CASING FOR ENDOSCOPES AND METHOD OF MAKING

[76] Inventor: Charles D. Cawood, 11527 N. Lou Al Ct., Houston, Tex. 77024

[21] Appl. No.: 349,247

[22] Filed: Dec. 5, 1994

[51] Int. Cl.⁶ .................................................. G02B 23/26
[52] U.S. Cl. ........................... 385/117; 385/147; 600/160
[58] Field of Search ...................................... 385/901, 115, 385/116, 117, 118, 119, 147; 128/4, 6

[56] References Cited

U.S. PATENT DOCUMENTS

| | | | |
|---|---|---|---|
| 3,261,349 | 8/1963 | Wallace | 128/6 |
| 3,261,356 | 7/1966 | Wallace | 128/276 |
| 3,498,286 | 3/1970 | Polanyi et al. | 128/2 |
| 3,556,086 | 1/1971 | Gordon | 128/22 |
| 3,691,001 | 9/1972 | Takahashi et al. | 385/115 |
| 3,944,341 | 3/1976 | Pomerantzeff | 351/7 |
| 4,664,486 | 5/1987 | Landre et al. | 385/117 |
| 4,802,460 | 2/1989 | Ohkuwa et al. | 128/6 |
| 4,846,154 | 7/1989 | MacAnally et al. | 128/6 |
| 5,046,816 | 10/1991 | Lehmann et al. | 385/117 |
| 5,369,525 | 11/1994 | Bala et al. | 385/117 |

FOREIGN PATENT DOCUMENTS

| | | | |
|---|---|---|---|
| 1956963 | 5/1970 | Germany | 385/115 |

*Primary Examiner*—Rodney B. Bovernick
*Assistant Examiner*—John Ngo
*Attorney, Agent, or Firm*—Tilton Fallon Lungmus

[57] ABSTRACT

An endoscope which provides ample illumination to a surgical field or diagnostic site is disclosed in which a lens train having objective and relay lenses for transmitting images therethrough is covered by an outer casing formed from a woven cylindrical sheath composed of a multiplicity of interlaced spirally-extending bundles of optical fibers and an embedding medium for securely interlocking the bundles together. The proximal end of the braided or woven sheath forms a light-receiving post for receiving and transmitting light through the individual fiberoptic cables to their distal ends which terminate around the periphery of the field lens or lenses. Constructing the outer casing of the endoscope from woven fiberoptic bundles provides an adequate quantity of fiberoptic cables to supply ample illumination to the field for endoscopes with one or more field lenses. The construction of the braided sheath also allows the endoscope to be efficiently manufactured. In an alternate embodiment, the outer casing is formed from a plurality of woven radial segments each composed of a multiplicity of interlaced spirally-extending bundles of optical fibers and an embedding medium securely interlocks the radial segments together to form the tubular outer casing.

31 Claims, 2 Drawing Sheets

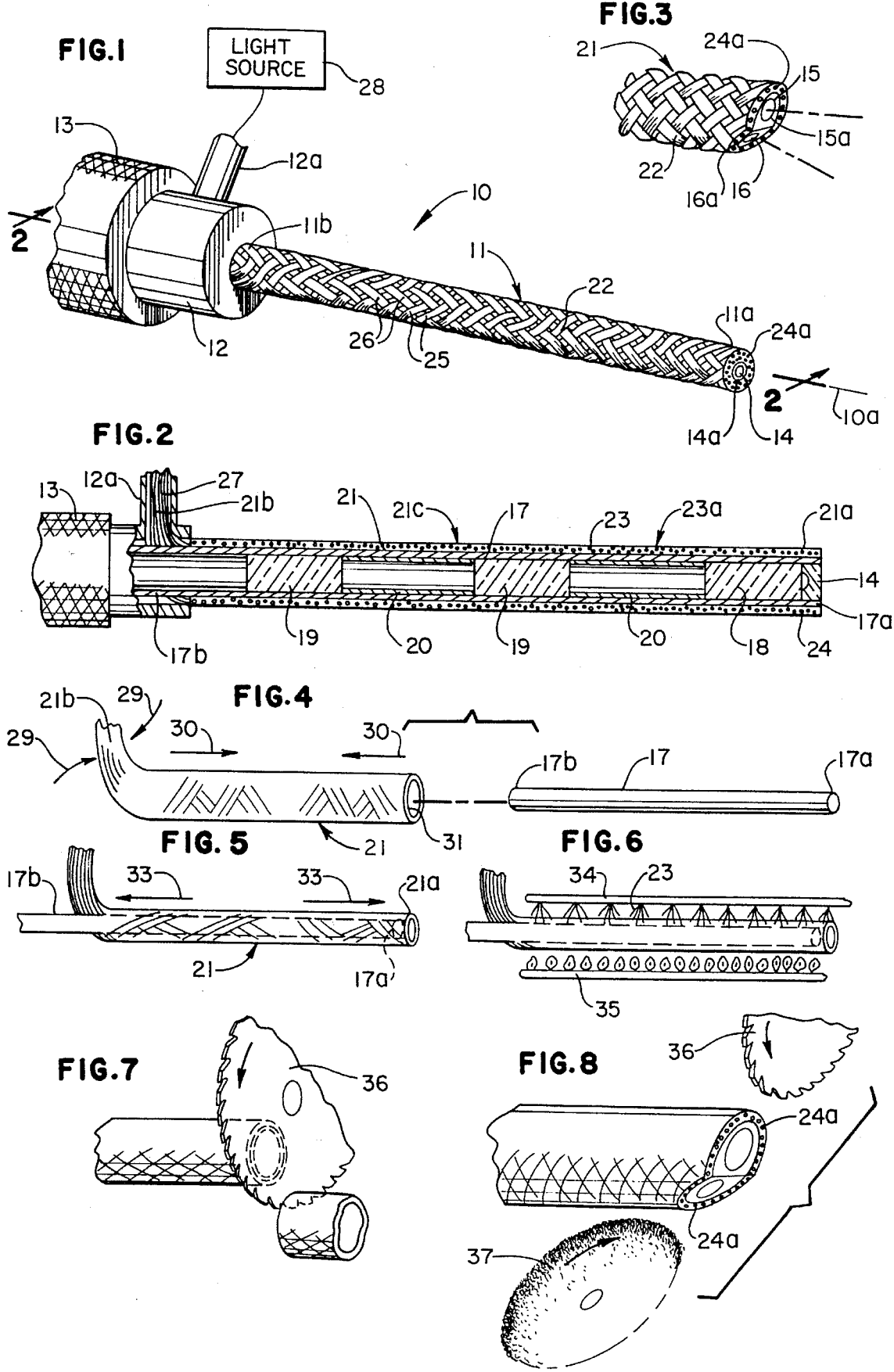

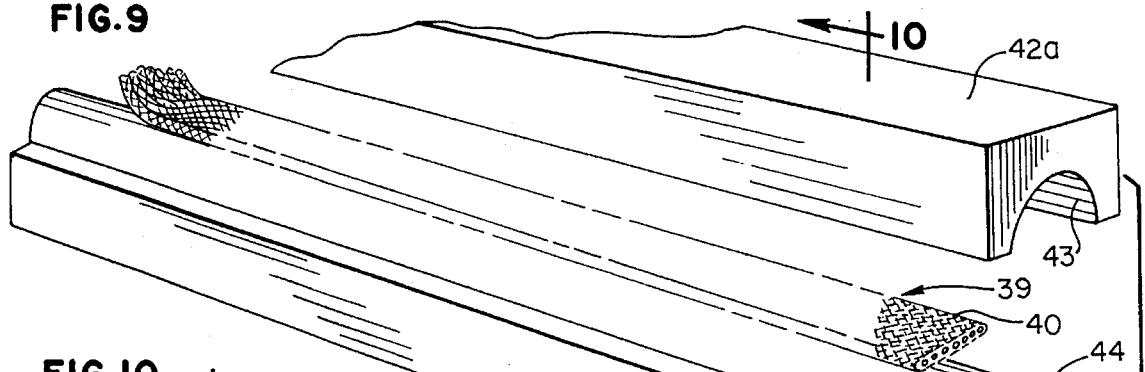
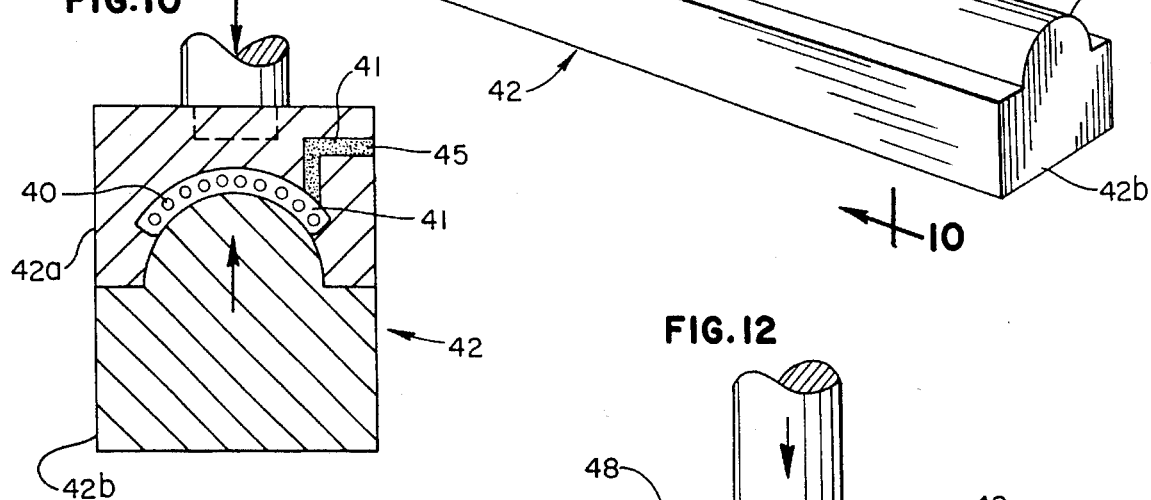
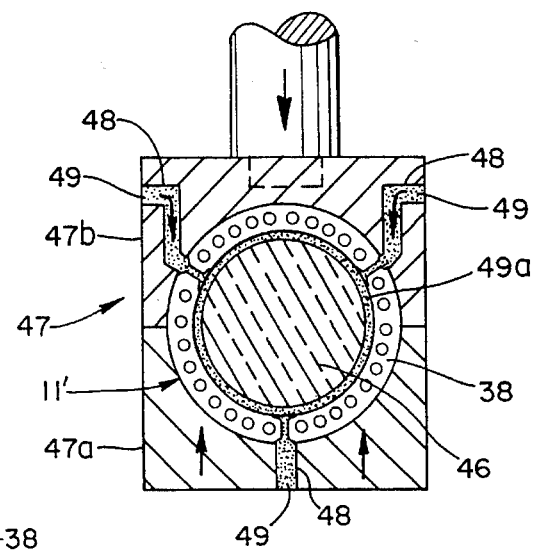
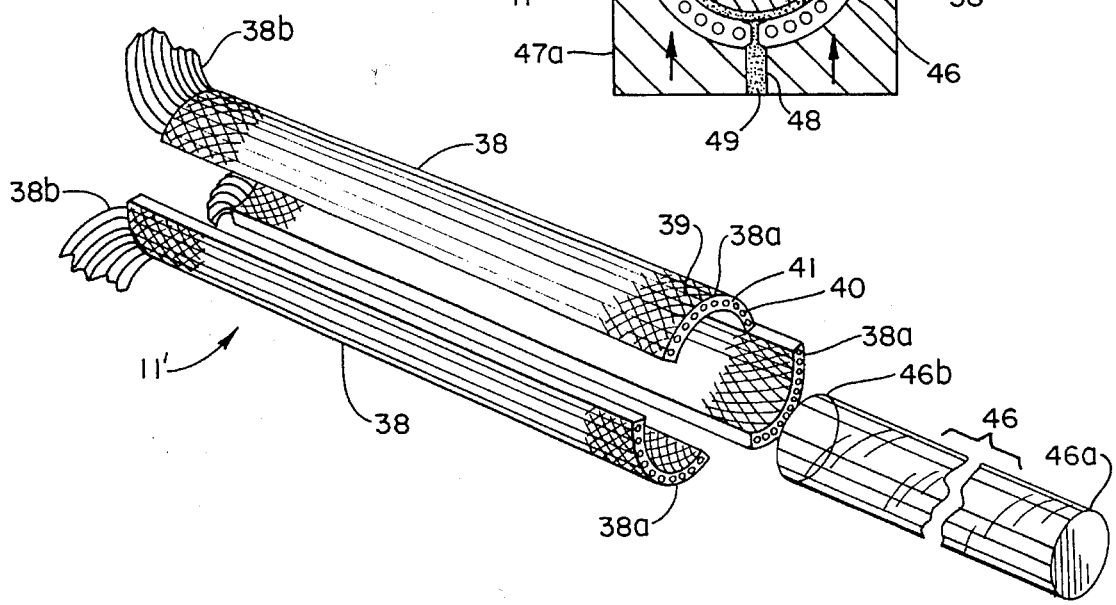

FIBEROPTIC CASING FOR ENDOSCOPES AND METHOD OF MAKING

BACKGROUND AND SUMMARY

Endoscopic instruments are widely known in which illumination of the field is provided by fiberoptic cables or bundles that transmit light through the barrel of the endoscope to its distal end and in which visual images are then transmitted back to the user through a series of lenses extending through the endoscope barrel from a field lens at the distal end to an eyepiece lens assembly at the endoscope's proximal end. Such endoscopes commonly include an outer tubular barrel, an inner barrel which houses a series of lenses for transmitting visual images through the endoscope, and fiberoptic cables or bundles positioned between the outer and inner barrels for transmitting light to the distal end of the endoscope and the adjacent field. See U.S. Pat. Nos. 5,046,816, 4,846,154, and 3,261,349. While such constructions provide sufficient illumination to the field in many instances, it has been found that such constructions do not provide adequate illumination to the field in some applications due to the limited quantity of fiberoptic cables or bundles which can be interposed between the outer and inner barrels without expanding the endoscope's diameter. This is particularly true in endoscopes which require greater illumination such as endoscopes having two field lenses for stereoscopic viewing or a first forwardly-directed field lens and a second laterally-directed field lens as disclosed in U.S. Pat. No. 4,846,154.

Attempting to include additional fiberoptic cables or bundles between the outer and inner barrels of such constructions is unrealistic because of diameter constraints as well as manufacturing cost and complexity. For example, it has been found that attempting to position large numbers of fiberoptic cables or bundles around an inner barrel while slipping an outer barrel over the fibers is exceedingly difficult to achieve without dislodging, damaging or otherwise misaligning the individual fiberoptic cables or strands.

An important aspect of this invention therefore lies in providing a relatively uncomplicated and efficiently manufacturable endoscope which provides ample illumination to the surgical or diagnostic field for endoscope's with one or more field lenses. Such results are achieved by eliminating the outer barrel from the endoscope and providing the endoscope with an outer casing around the inner barrel which is composed almost entirely of fiberoptic bundles. The fiberoptic bundles are interwoven together to form a braided sheath and a bonding means in the form of a curable embedding medium interlocks the bundles together and provides a relatively smooth outwardly-facing surface for the endoscope. Such a construction provides a greater number of fiberoptic cables in the endoscope than prior art devices without expanding the endoscope's diameter and provides ample illumination for endoscopes which may include more than one field lens. Such a construction also eliminates many of the manufacturing complexities encountered with prior art constructions.

In brief, the endoscope of this invention includes an elongated lens train having proximal and distal ends with an eyepiece lens assembly at its proximal end and at least one field lens at its distal end. The lens train includes objective and relay lens means for producing images and transmitting the same from the field lens or lenses back to the eyepiece lens assembly. An outer casing surrounds the lens train and includes a woven cylindrical sheath composed of a multiplicity of interlaced spirally-extending fiberoptic bundles or strands and a bonding means for maintaining the fiberoptic bundles in their configuration. The bonding means may take the form of a curable embedding medium composed of any of a number of well-known epoxy resins or other resins capable of being applied in liquid form and curing into a hardened state.

In a preferred form, the braided sheath includes a first spiral arrangement of a plurality of parallel fiberoptic bundles which are interwoven with an oppositely orientated, second spiral arrangement of a plurality of parallel fiberoptic bundles to form the braided tubular sheath. The proximal end of the sheath extends transversely outward from the inner barrel and forms a light-receiving post for receiving light from an external source and transmitting that light through the individual fiberoptic cables to their distal ends at the other end of the sheath. Those distal ends are exposed and surround the periphery of the field lens or lenses so that light transmitted therethrough illuminates the adjacent field.

Forming the outer casing of the endoscope from woven or interlaced spirally-extending fiberoptic bundles not only provides ample illumination of the field but is also advantageous in that the braided or woven structure imparts limited flexibility to the endoscope's barrel which is desirable in many applications. The spiral arrangement and opposite orientation of the two sets of fiberoptic bundles is also advantageous in that their distal ends terminate at angles to the barrel's longitudinal axis and provide improved light dispersion at the barrel's distal end and to the adjacent field.

Forming the endoscope's outer casing from the braided sheath also allows for efficient assembly of the endoscope. First, the braided or woven sheath is pre-assembled by interweaving together a plurality of fiberoptic bundles, each bundle including a plurality of individual fiberoptic cables. Preferably, the bundles are woven into a first spiral arrangement of a plurality of parallel fiberoptic bundles and a second similar, but oppositely oriented, spiral arrangement of fiberoptic bundles. The fiberoptic bundles may be woven together by known weaving methods commonly employed to form metal wire braided sheaths for coaxial cable or other known methods in the tubular textile manufacturing industry. The proximal end of the braided sheath is then formed into a light-receiving post that departs from the lens train and extends transversely thereto for connection to an external light source.

Once the tubular sheath is so formed, the sheath's diameter is expanded by pressing the distal and proximal ends together and the lens train is then inserted into the sheath. The lens train includes objective and relay lens means for transmitting images through the lens train and the proximal end of the lens train projects through an opening in the braided sheath for later connection to the eyepiece lens assembly. Thereafter the proximal and distal ends of the sheath are pulled apart to contract the sheath's diameter around the inner barrel so that the distal end of the sheath projects beyond a distal end of the inner barrel as well as the at least one field lens. Bonding means are then applied to the sheath for interlocking the fiberoptic bundles together and such bonding means may include a curable embedding medium composed of a well-known epoxy resin or other resin capable of being applied to the bundles in liquid form and then hardened or cured so that the endoscope barrel has a relatively smooth outwardly-facing surface. The distal end of the sheath is then severed around the periphery of the field lens or lenses to expose the distal ends of the individual fiberoptic cables. The exposed distal ends are then polished with an emery cloth or the like to allow transmission of light therethrough. The inner barrel is then connected at its proximal end to an eyepiece lens assembly and the light-receiving post is connected to an external light source for completing the endoscope.

In an alternate embodiment, the outer casing is formed from a plurality of elongated radial segments which are secured together by a bonding means to form the outer casing of the endoscope. Each of the segments includes a plurality of interlaced spirally-extending fiberoptic cables which are securely interlocked together by a bonding means such as a curable embedding medium. Such a construction is advantageous in that the embedding medium secures the segments to the lens train to prevent fluid ingress between the lens train and the outer casing.

Other advantages, features, and objects of the invention will become apparent from the specification and drawings.

BRIEF DESCRIPTION OF DRAWINGS

FIG. 1 is a perspective view of an endoscope having fiberoptic outer casing embodying this invention.

FIG. 2 is a sectional longitudinal view of the instrument.

FIG. 3 is an enlarged view of the distal end of one embodiment of the instrument having a first forwardly-facing field lens and a second laterally-facing field lens.

FIG. 4 is a schematic view illustrating the steps of expanding the tubular sheath's diameter and inserting the inner tubular barrel into the sheath.

FIG. 5 is a schematic view illustrating the steps of contracting the tubular sheath's diameter about the inner tubular barrel by drawing or longitudinally stretching the woven fibers.

FIG. 6 is a schematic view illustrating the sheath being coated with a bonding material and application of heat thereto.

FIG. 7 is a schematic view illustrating the step of cutting the distal end of the braided sheath to expose the distal ends of the individual fiberoptic cables around the periphery of a single field lens.

FIG. 8 is a schematic view illustrating the steps of cutting the distal end of the braided sheath to expose the distal ends of the individual fiberoptic cables around the forwardly-directed field lens and polishing the distal ends of the fiberoptic cables around the laterally-directed field lens.

FIG. 9 is a schematic perspective view illustrating the step of forming an elongated radial segment for use in an alternate embodiment of this invention.

FIG. 10 is a cross section of FIG. 9 illustrating the radial segment pressed between two forms and the application of a curable embedding medium.

FIG. 11 is a schematic perspective view illustrating a plurality of elongated radial segments arranged to form an outer casing around a lens train.

FIG. 12 is a schematic cross-sectional view illustrating the step of bonding the radial segments together with a curable embedding medium to form the outer casing.

DETAILED DESCRIPTION OF PREFERRED EMBODIMENTS

Referring to the drawings, the numeral 10 generally designates an endoscope having an elongated outer casing 11 with distal and proximal ends 11a and 11b, respectively. The proximal end of outer casing 11 is secured within tubular housing 12 to which a standard image-magnifying eyepiece lens assembly 13 is connected. The distal end of the endoscope is provided with at least one field lens 14 for viewing an external field adjacent to that end. Alternatively, the distal end may be provided with a first field lens 15 having a forwardly-directed orientation and a second field lens 116 having a laterally-directed orientation as illustrated in FIG. 3. A particularly advantageous endoscope that provides both forward and lateral viewing, and the details of its construction, are described in U.S. Pat. No. 4,846,154, which is hereby incorporated by reference. While the present invention is discussed herein primarily with respect to an endoscope having one field lens or both a forward and lateral lens, it will be understood that other configurations of one or more field lenses may be utilized with this invention such as providing two forwardly-directed adjacent field lenses for stereoscopic viewing of the field.

A lens train 17 is provided within outer casing 11 of the endoscope and includes objective and relay lens means for producing and transmitting images from the field lens or lenses back through the inner barrel and to eyepiece lens assembly 13. In the illustration given in FIG. 2, the lens train 17 includes an inner tubular barrel 17c, an objective lens 18 adjacent to field lens 14, and a series of relay lenses 19 which are spaced apart by tubular spacers 20, if required, within the inner barrel for proper transmission of images back to eyepiece lens assembly 13. It sill be understood other types of lens trains may be employed with this invention which may include a solid one-piece elongated lens train or a multiplicity of lens elements that are inserted into the outer casing. Preferably, the inner barrel 17c is omitted as it occupies valuable space in the endoscope. In the embodiments shown in the drawings, the lens train is shown as a one-piece assembly for ease of illustration and discussion. Eyepiece lens assembly 13 may be entirely conventional and includes a lens group for achieving a desired degree of magnification of the image.

Outer casing 11 is comprised of two main components: a braided or woven cylindrical sheath 21 composed of a plurality of interlaced fiberoptic bundles 22 and a bonding means, generally designated at 23, for interlocking the bundles together and forming a relatively smooth outwardly-facing surface 23a over the entirety of the outer casing. Depending upon the woven pattern of the woven sheath, the bonding means may be interspersed with the fiberoptic bundles or may primarily cover the outer surface of the sheath. Such bonding means may take the form of a curable embedding medium which is applied to the bundles in liquid form and then cured by application of heat or ultraviolet rays. Any one of a number of well-known and commercially available epoxy resins or other resins capable of being applied in liquid form and curing into a rigid or semirigid state may be selected for this purpose. Such embedding mediums are commercially available from Master Bond, Inc., Hackensack, N.J. Such materials are also generally opaque which is advantageous for covering the fiberoptic bundles. Preferably, the embedding medium is applied so that its interspersed with the fiberoptic cables and adheres to the lens train to form a fluid-tight seal therebetween which prevents fluid ingress between the fiberoptic outer casing and the lens train at the endoscope's distal end.

Each fiberoptic bundle 22 includes a plurality of individual fiberoptic cables 24 and a plurality of such bundles are interwoven together to form the woven tubular sheath which is illustrated schematically in FIGS. 4 and 5 without the bonding means. The woven pattern of the sheath is of the type commonly used with "Chinese-Finger Puzzles" which maintains the bundles in tubular or cylindrical configuration but allows expansion and contraction of the sheath's diameter by respectively pushing or pulling on the ends of the sheath. Such tubular woven patterns are also used for weaving metal wire casings, and the techniques for weaving such wire casings, or Chinese Finger Puzzles, may be employed for forming braided sheath 21. Atkins & Pearce of Covington, Ky., is one known manufacturing firm that specializes in braiding and weaving methods for manufacturing tubular textiles.

In a preferred woven pattern, a first spiral arrangement 25 is formed from a plurality of parallel fiberoptic bundles 22 which are spaced apart and follow a spiral pattern around lens train 17 such that the bundles extend in directions not parallel to a longitudinal axis 10a of endoscope 10. Similarly, a second spiral arrangement 26 is formed from a plurality of spaced and parallel fiberoptic bundles 22 which follow a spiral pattern which is oppositely orientated with respect to the spiral pattern of the first arrangement. The first and second arrangements of fiberoptic bundles are interwoven together and, as most clearly seen in FIG. 3, each fiberoptic bundle alternately passes over and under each of the successive fiberoptic bundles in the opposite arrangement to form a braided or woven pattern that maintains the bundles in their tubular configuration.

Braided sheath 21 has distal and proximal ends 21a and 21b and an elongated tubular portion 21c which is concentric with and extends along the length of lens train 17. The proximal end 21b of the braided sheath extends from lens train 17 in a generally transverse direction to form a light-receiving post 27 which is received in extension 12a from housing 12. Lightpost 27 is connected to a conventional light source 28 which provides light for transmission through the individual fiberoptic cables 24, and the distal ends 24a of the cables are exposed and polished to allow transmission of light therethrough for illuminating the external field.

As shown in the illustration given in FIG. 1, distal ends 24a of the fiberoptic cables surround the periphery 14a of field lens 14 for providing illumination to the field. The spiral orientation of the bundles results in each of the fiberoptic cables having an angled orientation to the endoscope's longitudinal axis which results in better light dispersal at the endoscope's distal end than if the fibers were directed along the endoscope's axis to act as point light sources. The crossing spiral pattern of the bundles also results in light from the oppositely orientated distal ends crossing which further provides enhanced light dispersal and full illumination of the field. Such a construction is particularly advantageous in a dual-view endoscope as shown in FIG. 3 in which more than one field lens is provided. As shown in that figure, distal ends 24a of the fiberoptic cables surround the peripheries 15a and 16a of field lenses 15 and 16 and the angled orientation of the fiberoptic cables provides improved light dispersal to each of the respective fields.

The method of constructing the endoscope of this invention first involves forming braided sheath 21 by interweaving first and second spiral arrangements 25 and 26 of fiberoptic bundles together using conventional methods commonly employed to interweave metal wire braided sheaths for coaxial cable or used to form Chinese-Finger Puzzles. Sheath 21 may be manufactured as a tubular article of indefinite length which is later cut into individual lengths each having an uncompressed length greater than the length of lens train 17. The proximal end 21b of the sheath is then compressed and bent, as schematically illustrated by arrows 29 in FIG. 4, to form light-receiving post 27 so that it extends transversely from the sheath for later positioning in housing 12.

The proximal and distal ends of the sheath are then pressed together as shown by arrows 30 to expand diameter 31 of the sheath to accommodate lens train 17. Lens train 17 is then inserted into the sheath so that its proximal end 17b protrudes through an opening 32 at the sheath's proximal end. Opening 30 may be preformed with a dowel or like tool which pushes aside the woven fiberoptic cables to allow lens train 17 to pass therethrough or may be formed upon insertion of lens train 17 by working the lens train's proximal end through the woven fiberoptic bundles.

As illustrated in FIG. 5, the distal and proximal ends 21a and 21b of the sheath are then pulled apart as illustrated by arrows 33 to contract the sheath's diameter about lens train 17 so that distal end 21a of the sheath projects beyond distal end 17b of lens train 17. Prior to that step, one or more field lenses should already be positioned in lens train 17 or may be externally attached to lens train 17 so that, when the sheath is tightened about the barrel, distal end 21a of the sheath projects beyond the end of the field lens assembly.

Once sheath 21 is tensioned to tightly surround the lens train, bonding means 23 are applied to the sheath by applicator 34 which spray coats or otherwise applies a curable embedding medium to the sheath. Preferably, the embedding medium penetrates the fiberoptic cables and adheres to the lens train for providing an effective seal at the endoscope's distal end. Then, heat application station applies heat to the medium to cure or harden it. When it is desirable to use a resin which is curable by application of ultraviolet rays instead of heat, heat applying station 35 may take the form of a bank of ultraviolet lights.

Once the outer casing is fully cured or hardened, the excess portion of sheath 21 that projects beyond the field lens assembly is severed with suitable cutting means, schematically illustrated at 36, to expose the distal ends 24a of the fiberoptic cables 24 around the periphery of the field lens or lenses as illustrated in FIGS. 7 and 8. Such cutting means may take the form of a blade, file or the like as fiberoptic cables are typically easy to sever. After the severing step, the distal ends of the fiberoptic cables are polished with an emery cloth 37 or suitable polishing material for allowing transmission of light through the distal ends and into the field. To complete assembly, the endoscope barrel is then attached to housing 12 by connecting lens train 17 to eyepiece assembly 13, connecting light-receiving post 27 to housing 12, and sealing the assembly in a conventional manner as is well-known in the art.

FIGS. 9–12 illustrate an alternate embodiment of this invention in which the outer casing 11' of the endoscope includes a plurality of elongated radial segments 38 each composed of a web 39 formed from individual fiberoptic cables 40 and a bonding means 41 (FIG. 11) for securing the cables together. In the illustration given in FIG. 9, web 39 is formed from a plurality of interlaced or woven spirally-extending fiberoptic cables 40 and the web is initially woven to have a generally flat elongated configuration. The woven configuration of the web is flexible and allows the webs to conform to a radial shape.

The radial segments 38 are formed by a press 42 having plates 42a and 42b, and plates 42a and 42b, respectively, include a radial indentation 43 and a radial projection 44. When the plates are pressed together, the flexible woven web conforms to a radial shape as illustrated in FIG. 10. Bonding means 41 are then applied to the web for securely interlocking the fiberoptic cables 40 together in the radial configuration. The bonding means may comprise a curable embedding medium or resin as previously described and may be injected through a gate 45 for application to the fiberoptic cables. Alternatively, top press 42a may be removed and the bonding means may be applied by spraying as illustrated in FIG. 6. The bonding means is then cured with heat or ultraviolet light as previously discussed.

Once cured, the radial segments 38 have a semi-rigid or rigid construction and segments 38 are illustrated in their finished form in FIG. 11. In the illustration given, three radial segments form the tubular outer casing but it will be understood that any number of two or more radial segments may be used to form the tubular outer casing. Segments 38 each have a distal and proximal end 38a and 38b. Preferably, the proximal ends 38b of the segments are composed of fiberoptic cables which are free of the bonding means so that they may be later formed into a light-receiving post as previously discussed. The distal ends 38a of the segments may be precut as shown to expose the distal ends of the individual fiberoptic cables and the exposed distal ends may be polished for allowing the transmission of light therethrough to an adjacent field. When the segments are affixed to a lens train 46, the distall ends of the segment are positioned substantially flush with the distal end 46a of the lens train. In the alternative, the segments and lens train may be assembled so that the distal ends 38a of the segments project beyond the distal end 46a of the lens train and the distal ends of the segments are then severed and polished as previously discussed in connection with FIGS. 7 and 8.

Assembly of the outer casing 11' from radial segments 38 is shown in FIG. 12. In particular, radial segments 38 are arranged around lens train 46 in a clamping jig 47 having a bottom half 47a and a top half 47b. Clamping jig 47 defines a plurality of gates 48 through which bonding means 49 are injected to secure the elongated edges of the segments together to form the tubular outer casing. The bonding means 49 may comprise a curable embedding medium as previously discussed. Preferably, the bonding means 49 are applied so that a thin layer 49a of resin is formed between the radial segments and the lens train to prevent fluid ingress between the radial segments and the lens train. It will be understood that other methods of applying the second bonding means to the segments and the lens train may be also used for forming the tubular outer casing. Once the tubular outer casing is complete, the proximal end 46b of the lens train is connected to the eyepiece lens assembly and the proximal ends 38b of the segments are connected to the light post as previously discussed to complete the endoscope.

While in the foregoing embodiments of this invention have been disclosed in considerable detail for purposes of illustration, it will be understood that many of these details may be varied without departing from the spirit and scope of the invention.

I claim:

1. An endoscope comprising:

a lens train having proximal and distal ends with an eyepiece lens assembly at said proximal end and at least one field lens at said distal end, said lens train including objective and relay lens means for producing images and transmitting the same from said at least one field lens to said eyepiece assembly;

a tubular outer casing concentric with and extending along said lens train and including a woven cylindrical sheath composed of a plurality of interwoven spirally-extending fiberoptic bundles, each bundle including at least one fiberoptic cable, and bonding means for interlocking said fiberoptic bundles together;

said woven sheath having a proximal end which extends transversely outward from said lens train and forms a light-receiving post for receiving and transmitting light through each of said fiberoptic cables and having a distal end which includes exposed distal ends of said fiberoptic cables positioned about a periphery of said at least one field lens for illuminating an adjacent field.

2. The endoscope of claim 1 in which said braided sheath includes a first spiral arrangement composed of a plurality of said fiberoptic bundles which are interwoven with an oppositely orientated, second spiral arrangement composed of a plurality of said fiberoptic bundles.

3. The endoscope of claim 2 in which said fiberoptic bundles in said first spiral arrangement are parallel to each other and said fiberoptic bundles in said second spiral arrangement are parallel to each other.

4. The endoscope of claim 1 in which said distal ends of said fiberoptic cables extend in directions not parallel to a longitudinal axis of said endoscope.

5. The endoscope of claim 1 in which two field lenses are positioned at said distal end of said lens train.

6. The endoscope of claim 5 in which one of said two field lenses has a forwardly-directed orientation and the other of said field lenses has a laterally-directed orientation.

7. The endoscope of claim 1 in which said bonding means comprises a curable embedding medium.

8. The endoscope of claim 7 in which said bonding means comprises a resin.

9. The endoscope of claim 1 in which said lens train is disposed in an inner tubular barrel.

10. A method of making an endoscope with a fiberoptic outer casing comprising the steps of:

interweaving a first and second arrangement of a plurality of fiberoptic bundles to form an elongated tubular braided sheath having proximal and distal ends, each of said fiberoptic bundles including a plurality of individual fiberoptic cables;

forming said proximal end of said braided sheath into a light-receiving post;

pressing said proximal end of said distal ends of said braided sheath towards each other to expand a diameter of said braided sheath;

then, inserting an elongated lens train into said braided sheath so that a proximal end of said lens train projects through an opening at said proximal end of said braided sheath;

thereafter, pulling said proximal and distal ends of said braided sheath apart to contract the diameter of said braided sheath around said lens train so that said distal end of said braided sheath projects beyond a distal end of said lens train, said distal end of said lens train including at least one field lens;

applying a bonding means to said braided sheath for securely interlocking said first and second arrangements of fiberoptic bundles together and then curing or hardening said bonding means;

then, severing said distal end of said braided sheath to expose distal ends of said individual fiberoptic cables around a periphery of said at least one field lens; and polishing said distal ends of said fiberoptic cables for allowing transmission of light therethrough.

11. The method of claim 10 comprising the further step of connecting said light-receiving post to an external light source and connecting said proximal end of said lens train to a eyepiece assembly.

12. The method of claim 10 in which said distal end of said lens train includes a first forwardly-directed field lens and a second laterally-directed field lens and said steps of severing and polishing the distal ends around both said first and second field lenses.

13. The method of claim 10 in which said fiberoptic bundles in said first arrangement are parallel and spaced apart and follow a spiral pattern in a direction not parallel to a longitudinal axis of said endoscope and said fiberoptic bundles in said second arrangement are parallel and spaced apart in a direction not parallel to said longitudinal axis.

14. The method of claim 10 in which said bonding means comprises a curable embedding medium.

15. The method of claim 10 is which said bonding means comprises a resin.

16. The method of claim 14 in which said curing step is performed by applying heat or ultraviolet rays to said medium.

17. An endoscope comprising:

a lens train having proximal and distal ends with an eyepiece lens assembly at said proximal end and at least one field lens at said distal end, said lens train including objective and relay lens means for producing images and transmitting the same from said at least one field lens to said eyepiece lens assembly;

a tubular outer casing concentric with and extending along said lens train and including a plurality of elongated radial segments and first bonding means for interlocking said segments together about said lens train, each of said segments including a web formed from a plurality of fiberoptic cables and second bonding means for interlocking said cables together;

said segments having proximal ends which extend transversely outward from said lens train and form a light-receiving post for receiving and transmitting light through each of said fiberoptic cables and having distal ends which include exposed distal ends of said fiberoptic cables positioned about a periphery of said at least one field lens for illuminating an adjacent field.

18. The endoscope of claim 17 in which said fiberoptic cables in said webs are interlaced and extend in directions not parallel to a longitudinal axis of said endoscope.

19. The endoscope of claim 17 in which two field lenses are positioned at said distal end of said lens train.

20. The endoscope of claim 19 in which one of said field lenses has a forwardly-directed orientation and the other of said field lenses has a laterally-directed orientation.

21. The endoscope of claim 17 in which said first and second bonding means comprises a curable embedding medium.

22. The endoscope of claim 21 in which said bonding means comprises a resin.

23. A method of making an endoscope with a fiberoptic outer casing comprising the steps of:

interweaving a plurality of fiberoptic cables to form a plurality of elongated webs;

forming said webs to have a radial configuration;

applying bonding means to said webs for securely interlocking said fiberoptic cables together;

then, curing or hardening said bonding means so that said webs and said binding means form a plurality of radial segments;

then, positioning said radial segments so that they extend along the length of a lens train and form a tubular outer casing, said lens train having proximal and distal ends and including at least one field lens at said distal end; and thereafter, applying bonding means to said radial segments for securely interlocking said segments together about said lens train and then curing or hardening said bonding means.

24. The method of claim 23 in which distal ends of said segments extend beyond said distal end of said lens train and said method further comprises the step of severing said distal ends of said segments to expose distal ends of said individual fiberoptic cables about a periphery of said at least one field lens; and then, polishing said distal ends of said fiberoptic cables for allowing transmission of light therethrough.

25. The method of claim 24 in which said distal end of said lens train includes a first forwardly-directed field lens and a second laterally-directed field lens and said steps of severing and polishing the distal ends of said fiberoptic cables includes severing and polishing the distal ends around both said first and second field lenses.

26. The method of claim 23 in which said segments include proximal ends formed of said fiberoptic cables which are free of said bonding means and said method further comprises the step of forming said proximal ends of said segments into a light-receiving post.

27. The method of claim 26 comprising the further step of connecting said light-receiving post to an external light source and connecting said proximal end of said lens train to an eyepiece assembly.

28. The method of claim 23 in which said step of applying said bonding means to said segments includes applying said bonding means between said radial segments and said lens train to form a fluid-tight seal between said radial segments and said lens train.

29. The method of claim 23 in which said fiberoptic cables extend in directions not parallel to a longitudinal axis of said endoscope.

30. The method of claim 23 in which said bonding means comprise a curable embedding medium.

31. The method of claim 30 in which said curable embedding medium comprises a resin.

* * * * *